(12) United States Patent
Nuotio et al.

(10) Patent No.: US 10,335,792 B2
(45) Date of Patent: Jul. 2, 2019

(54) REAGENT BOTTLE CAP, SYSTEM, METHOD AND APPARATUS FOR HANDLING CLOSURE CAPS AND LIKE

(71) Applicant: Thermo Fisher Scientific Oy, Vantaa (FI)

(72) Inventors: Vesa Nuotio, Vantaa (FI); Olli Myyryläinen, Vantaa (FI)

(73) Assignee: THERMO FISHER SCIENTIFIC OY, Vantaa (FI)

(*) Notice: Subject to any disclaimer, the term of this patent is extended or adjusted under 35 U.S.C. 154(b) by 664 days.

(21) Appl. No.: 14/263,336

(22) Filed: Apr. 28, 2014

(65) Prior Publication Data

US 2014/0224382 A1 Aug. 14, 2014

Related U.S. Application Data

(63) Continuation-in-part of application No. PCT/FI2012/050998, filed on Oct. 17, 2012.
(Continued)

(30) Foreign Application Priority Data

Oct. 28, 2011 (FI) ..................................... 20116059

(51) Int. Cl.
  *B01L 3/00* (2006.01)
  *B67B 7/00* (2006.01)
  (Continued)

(52) U.S. Cl.
  CPC ............... *B01L 3/523* (2013.01); *B67B 7/00* (2013.01); *G01N 35/1002* (2013.01);
  (Continued)

(58) Field of Classification Search
  CPC ...... B01L 3/523; B01L 2200/025; B67B 7/00; G01N 35/1002; G01N 2035/0405; G01N 2035/1051; G01N 2035/1048; B65D 5/708
  See application file for complete search history.

(56) References Cited

U.S. PATENT DOCUMENTS 1,860,954 A * 5/1932 Risser .................... B67B 3/2033
  53/302
2,021,259 A * 11/1935 Magnuson ............. B65D 39/12
  215/361
(Continued)

FOREIGN PATENT DOCUMENTS

CA    2 520 921 A1    10/2004
CH      624312 A5 *    7/1981 ............ B01L 3/0279
(Continued)

OTHER PUBLICATIONS

International Search Report issued in corresponding PCT Appliation No. PCT/FI2015/050240 dated Jul. 9, 2015 (in English).

*Primary Examiner* — Alexander M Valvis
*Assistant Examiner* — Lucas E. A. Palmer
(74) *Attorney, Agent, or Firm* — Birch, Stewart, Kolasch & Birch, LLP

(57) ABSTRACT

A reagent bottle includes an outer cap and an inner closing cap. The inner closing cap has a recess for gripping the cap. In addition, a system for handling closures is provided wherein a method removes a closing cap from a reagent bottle and a related gripper.

7 Claims, 13 Drawing Sheets

Related U.S. Application Data

(60) Provisional application No. 61/552,470, filed on Oct. 28, 2011.

(51) Int. Cl.
  *G01N 35/10* (2006.01)
  *B65D 5/70* (2006.01)
  *G01N 35/04* (2006.01)

(52) U.S. Cl.
  CPC ......... *B01L 2200/025* (2013.01); *B65D 5/708* (2013.01); *G01N 2035/0405* (2013.01); *G01N 2035/1051* (2013.01)

(56) References Cited

U.S. PATENT DOCUMENTS

| | | | | |
|---|---|---|---|---|
| 3,444,742 A * | 5/1969 | Ellis | B01L 3/021 | 422/922 |
| 3,628,307 A * | 12/1971 | Croasdale | B65B 7/2807 | 53/299 |
| 4,151,750 A * | 5/1979 | Suovaniemi | A61M 5/3205 | 422/932 |
| 4,244,915 A * | 1/1981 | Boardman | B29C 51/22 | 264/551 |
| 4,338,764 A * | 7/1982 | Percarpio | A61B 5/15003 | 53/432 |
| 4,399,711 A * | 8/1983 | Klein | B01L 3/0217 | 73/864.16 |
| 4,830,832 A * | 5/1989 | Arpagaus | B01L 3/0217 | 422/509 |
| 5,223,227 A * | 6/1993 | Zuckerman | G01N 11/162 | 422/547 |
| 5,452,619 A * | 9/1995 | Kawanabe | G01N 33/491 | 73/863 |
| 5,525,302 A * | 6/1996 | Astle | B01L 3/0279 | 422/511 |
| 5,750,881 A * | 5/1998 | Dorenkott | G01F 11/021 | 422/160 |
| 5,846,489 A * | 12/1998 | Bienhaus | B01L 3/50825 | 422/562 |
| 5,919,706 A * | 7/1999 | Tajima | G01F 23/292 | 422/106 |
| 6,017,698 A * | 1/2000 | Bienhaus | B01L 3/5082 | 422/255 |
| 6,216,340 B1 | 4/2001 | Fassbind et al. | | |
| 6,269,977 B1 | 8/2001 | Moore | | |
| 6,363,802 B1 * | 4/2002 | Grippo | G01N 35/1011 | 73/864.24 |
| 6,398,281 B1 * | 6/2002 | Heimberg | G01N 35/00 | 294/100 |
| 6,532,837 B1 * | 3/2003 | Magussen, Jr. | B01L 3/0279 | 73/864.01 |
| 7,347,338 B2 * | 3/2008 | Korpela | B01L 3/50825 | 215/355 |
| 7,513,857 B2 * | 4/2009 | Gueller | G01N 35/0099 | 222/504 |
| 7,666,357 B2 * | 2/2010 | Sattler | B01L 3/50825 | 422/547 |
| 8,163,256 B2 * | 4/2012 | Cote | B01L 3/0279 | 422/501 |
| 8,205,413 B2 * | 6/2012 | Kramer | G01N 35/04 | 53/331.5 |
| 8,357,538 B2 * | 1/2013 | Self | B01L 9/06 | 422/63 |
| 8,512,650 B2 * | 8/2013 | Jungheim | B01L 3/0275 | 422/511 |
| 8,986,614 B2 * | 3/2015 | Zhou | B01L 3/502738 | 422/502 |
| 9,073,052 B2 * | 7/2015 | Maslana | B01L 3/021 | |
| 2002/0095998 A1 * | 7/2002 | Kriz | B01L 3/0224 | 73/864.18 |
| 2003/0026738 A1 * | 2/2003 | Everett | B01L 3/5025 | 422/536 |
| 2004/0187441 A1 * | 9/2004 | Cirio | B67B 3/18 | 53/432 |
| 2006/0150789 A1 * | 7/2006 | Russell | B67B 7/20 | 83/30 |
| 2006/0211080 A1 * | 9/2006 | Frost, III | B01F 13/0052 | 435/30 |
| 2007/0119121 A1 * | 5/2007 | Woods | B65B 3/003 | 53/268 |
| 2008/0014610 A1 * | 1/2008 | Kamata | B01L 3/502 | 435/69.1 |
| 2008/0247914 A1 * | 10/2008 | Edens | G01N 35/0099 | 422/400 |
| 2008/0276758 A1 * | 11/2008 | Itoh | B67B 7/20 | 81/3.47 |
| 2008/0296297 A1 | 12/2008 | Ohashi | | |
| 2010/0126286 A1 * | 5/2010 | Self | G01N 35/04 | 73/863.81 |
| 2010/0181330 A1 * | 7/2010 | Quasters | B67C 3/223 | 220/795 |
| 2010/0236198 A1 | 9/2010 | Krämer et al. | | |
| 2010/0313688 A1 | 12/2010 | Hiltbrand | | |
| 2010/0322826 A1 * | 12/2010 | Locascio | B01J 19/0093 | 422/537 |
| 2011/0104742 A1 * | 5/2011 | Fox | G01N 35/0095 | 435/30 |
| 2011/0143452 A1 * | 6/2011 | Che | A01N 1/0268 | 436/180 |
| 2011/0239791 A1 | 10/2011 | Fici | | |
| 2012/0096819 A1 * | 4/2012 | Piepereit | B65B 7/2842 | 53/510 |
| 2012/0291872 A1 * | 11/2012 | Brady | G01N 35/1065 | 137/3 |
| 2013/0095508 A1 * | 4/2013 | Campitelli | B01L 3/0217 | 435/7.94 |
| 2013/0121878 A1 * | 5/2013 | Wilson | B01L 3/523 | 422/68.1 |
| 2014/0260118 A1 * | 9/2014 | Knight | B01L 3/50825 | 53/492 |

FOREIGN PATENT DOCUMENTS

| | | | |
|---|---|---|---|
| EP | 0 028 411 A1 | 5/1981 | |
| EP | 0557828 A1 * | 9/1993 | B67B 7/182 |
| EP | 0 571 100 A1 | 11/1993 | |
| EP | 0571100 A1 * | 11/1993 | G01F 23/14 |
| EP | 0 676 643 A2 | 10/1995 | |
| EP | 0 542 295 B1 | 4/1997 | |
| EP | 0 909 584 A2 | 4/1999 | |
| EP | 1 010 635 A3 | 6/2000 | |
| EP | 1 495 747 A1 | 1/2005 | |
| EP | 2 030 688 A1 | 3/2009 | |
| EP | 2 371 456 A1 | 10/2011 | |
| JP | 8-313535 A | 11/1996 | |
| JP | 2002-019855 A | 1/2002 | |
| JP | 2004-157020 A | 6/2004 | |
| WO | WO 2006/066056 A2 | 6/2006 | |
| WO | WO 2013/068636 A1 | 5/2013 | |

\* cited by examiner

REAGENT BOTTLE CAP, SYSTEM, METHOD AND APPARATUS FOR HANDLING CLOSURE CAPS AND LIKE

CROSS REFERENCE TO RELATED APPLICATIONS

This application is a Continuation-In-Part of PCT International Application No. PCT/FI2012/050998 filed on Oct. 17, 2012, which claims the benefit of U.S. Provisional Application No. 61/552,470 filed on Oct. 28, 2011 and priority under 35 U.S.C § 119(a) to Patent Application No. 20116059 filed in Finland on Oct. 28, 2011, all of which are hereby expressly incorporated by reference into the present application.

The present invention concerns reagent bottles, caps and a method for handling closure caps, for example for opening and closing said bottle and a related system, method and an apparatus for handling the closure caps and at least a pipette tip.

BACKGROUND ART

To prevent evaporation in reagent bottles the bottles have to be closed in storage area when not in use. They also have to be easily opened before the dispensing probe goes in to bottle to aspirate the reagent. After dispensing the bottle has to be reliably closed again.

Reagent containers used with clinical and laboratory analyzers are generally closed using caps and closures that have been developed in order to keep the contents of the containers uncontaminated or prevent evaporation. Many of the solutions contain piercable septums. Piercing these closures may, however, cause contamination of both dispensers and container contents, since it often is the edge of the dispenser needles that is used for the piercing, whereby the dispenser will come into contact with the closure each time it is used.

EP 0 542 295 concerns a stopper fitted on the mouth of a drug vessel body, which stopper is composed of a stopper body of an elastomeric material and has a hole passing therethrough along its center axis, and a closing body fitted in the hole of said stopper body, said closing body being in the form of a spherical member with a diameter greater than that of said hole, and said closing body being opened just before use using an unpointed end of a separate member for forcing the closing body in the hole to push in the vessel body.

EP 1 010 635 presents a pot-shaped cap comprising a lid portion and a skirt portion to be securely attached to a closed container neck of a drug container, with at least two puncture openings being provided in the lid portion of the cap, and a seal, which is made of an elastic material and covers the puncture openings, being located in the lid portion, said seal being inserted in a chamber integrally formed with the lid portion, said chamber protruding outwardly over the outside of the lid portion and said seal being disk-shaped.

JP 8313535 presents a plug body mounted on the mouth section of a container, which plug body contains a hole for passing a pipette meant to suck up a reagent from the reagent container and discharge it into a reaction container.

JP 2004157020 concerns a reagent container comprising a cap that is fitted to the opening of the container and that is made of an elastic material. The cap has a cross-like cut, which can be deformed by pressing and inserting a guide pipe into the cut from the outside.

Another type of closures essentially consists of two structures, one of which being the skirt that surrounds the opening of the vessel, keeping the closure in place, the other structure forming the lid, covering the opening of the vessel and being attached to the first structure by a spring. These types of closures have the disadvantage of requiring much free space around the vessel when being opened to allow the entire lid structure to move in the required direction.

EP 0 909 584 describes a cap for a reagent container, which is provided with a scalable lid, which lid can be pivoted laterally upward from the cap sealing position, with the container being opened, by means of an inclined bistable hinge, and which lid bears one or more catches, which can come into contact with an apparatus for opening or closing the lid.

A further type of closures contains a complex combination of elements meant to prevent evaporation, leakage of liquids and contamination.

CA 2 520 921 describes a dispensing assembly to be coupled to a vessel, the assembly containing a tip that includes a valve to allow drop-wise liquid dispensing, a vent opening, a filtration element and an antibacterial liner enabling the solution in the vessel to remain sterile.

U.S. Pat. No. 6,269,977 concerns a container cover consisting of a single molded disc shaped device with an elevated flat surface functioning as a platform for supporting another container thereon.

JP 2002019855 describes an adapter for preventing the liquid in a container from coming into contact with air, the adapter containing an opened upper part and a closed bottom part, the bottom further including a cut from which the liquid carp can be separately taken.

EP 1 495 747 presents a liquid drug container with a nozzle member and a nozzle cap, wherein the nozzle hole of the nozzle member is covered with a hydrophilic filter, and a top wall of the nozzle member is provided with an air hole covered with a hydrophobic filter.

The disadvantages of conventional closures include that in order to provide a solution that prevents evaporation and contamination, a very complex closure with several separate components is used. These complex solutions still do not focus on preventing contamination caused by contact between the closure and the dispenser, only between the inside of the vessel and the environment. The solutions of the prior art also fail in providing vessel closures that allow the dispensing devices to function without ever touching the vessels or the closures.

A reliable method for handling closure caps of liquid containers or other devices like pipette tips needed for transport and storage of liquids used during analyses using automated analyzing apparatuses has not been available. The apparatuses and methods in use utilize complicated robotic gripers, which provide great flexibility but are unnecessarily complicated and expensive and possibly difficult to keep clean.

For the above reasons, it would be beneficial to provide a reagent bottle and a cap that can be easily opened and closed in order to prevent evaporation and contamination of the reagent when in storage and to provide free access through the mouth of the bottle to the contents of the reagent bottle.

Further in order to provide reliable automated handling of the reagent bottle caps or other closures of liquid containers used in automated analyzing apparatuses as well as liquid handling devices like pipette tips, a novel system, method and apparatus should be provided.

SUMMARY

In a first aspect, the invention relates to a reagent bottle and a cap that can be easily attached and detached.

One embodiment of the invention allows use of a gripper means that include a pipette mount.

According to second aspects and embodiments of the present invention, the invention provides method for detaching a cap of a reagent bottle.

According to one embodiment of the invention, the invention provides method for gripping the cap.

According to one embodiment of the invention, the invention provides a method for sensing a connection of gripper and cap.

According to one embodiment of the invention, the invention provides a method for detaching the cap from the gripper.

According to one embodiment of the invention, the invention provides a method for sensing lack of connection between the cap and the gripper.

In a further aspect, the invention relates to a gripper for detaching and attaching the cap of a reagent bottle.

One embodiment of the invention provides a gripper for gripping aspirating means such as pipette.

One embodiment of the invention provides a system comprising closure or cap, at least one liquid handling device and a gripper for picking, transport and release of the closure, cap and liquid handling device.

The invention is based on fitting a reagent bottle with a removable cap having an inner recess extending into the cap and having an open end and a closed end, the recess being provided for gripping said cap, and a lip surrounding at least partially the recess.

According to one embodiment of the invention, the recess has a circular cross section.

According to one embodiment of the invention, the recess is preferably conical so that its dimensions in cross section decrease towards the closed end of the recess.

According to one embodiment, at least the lip comprises magnetic material so that the cap can be grabbed by a magnet.

According to one embodiment, the magnetic material is ferromagnetic material, in particular ferromagnetic metal.

According to one embodiment of the invention, the magnetic material is a ring placed on top of the cap of the bottle and surrounding the mouth of the bottle.

According to one embodiment of the invention the cap of the bottle has a closed recess that extends inside the mouth of the bottle.

The method according to the invention is based on providing the closure or cap and the liquid handling device a similar gripping interface so that they can be picked and released with a same gripper. Advantageously this is performed directly without using any separate adapters between the parts.

According to one preferred embodiment the gripping interface is a recess and a protruding mount, the outer surface of the mount and the inner surface of the recess being dimensioned so that they form a cone joint.

One embodiment of the method according to the invention is based on forming a friction contact between the cap of the reagent bottle or closure of another liquid vessel and detaching the cap by lifting it with the protruding mount of the gripper.

One embodiment of the method according to the invention is based on forming a magnetic contact between the cap of the reagent bottle or closure of another liquid vessel and detaching the cap by lifting it with the magnetic force of the gripper.

One embodiment of the method according to the invention is based on forming a negative pressure between the cap of the reagent bottle or closure of another liquid vessel and the gripper and detaching the cap by lifting it with the suction force of the gripper.

One embodiment of the gripper according to the invention is based on providing a fluid connection within the gripper mount for aspirating means that can be connected to the gripper for aspirating fluid by a fluid handling device, for example by a pipette tip.

One embodiment of the gripper comprises an electric magnet for generating magnetic field for gripping ferromagnetic contact element and providing a fluid connection within the electric magnet for aspirating means that can be connected to the gripper.

One embodiment of the gripper comprises a vacuum pad for sealing a negative pressure between a cap or closure and a pipette tip mount.

The system for handling closures, caps and liquid transport devices comprise at least one of the closure or cap, at least one liquid handling device and a gripper comprising a gripping interface that can be attached both to the closure or cap and the liquid handling device.

According to one aspect of the invention, the gripping interface is a cone joint.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

DETAILED DESCRIPTION OF EXEMPLARY EMBODIMENTS

Figure 1:
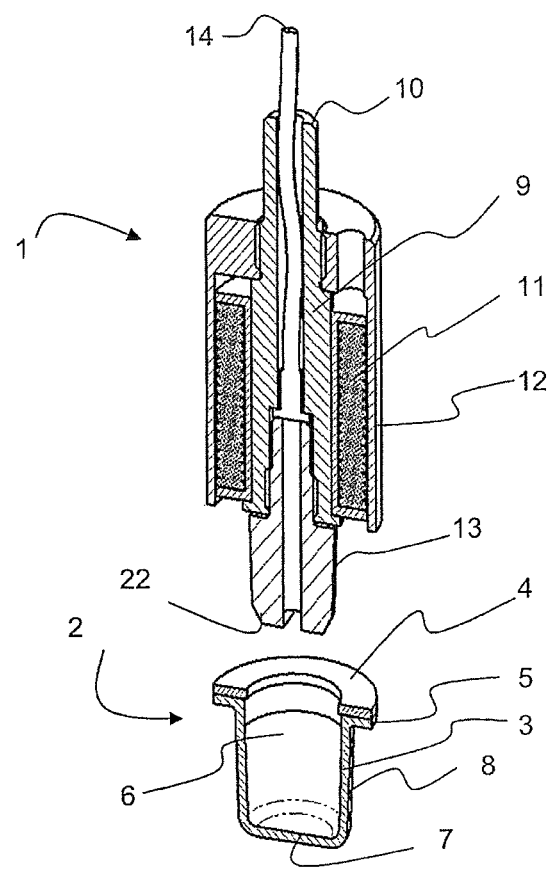
FIG. 1 shows one embodiment of a gripper.

FIG. 1 shows one embodiment of a gripper 1 and a cap 2. The cap herein comprises a metal washer 4 and a sealing cup that has a lip 5 that is dimensioned to correspond with the flat surface of the washer 4 and attaches the cup 3 to the washer 4. The cup has an inner recess 6 having a same diameter as the hole in the washer 4 and a closed bottom. The outer surface 8 of the cup 5 has to correspond with the dimensions of the mouth of the bottle it is supposed to seal. The metal washer can be made of any magnetic material like a ferromagnetic metal or a composite material comprising enough ferromagnetic material to react to a magnetic field. For example, polymers embedded with magnetic material could be used. The material of the cup part is supposed to provide sufficient seal on the bottle mouth and provide easy enough removability from the mouth. Various polymers provide suitable properties for making the cup part. It can even be contemplated that the cup is made of single part of polymer embedded with magnetic material.

The body of the gripper 1 is made of a metallic core 9 that has a central hole 10. Since the purpose of the core is to provide magnetic field, it should be made of materials used for cores of electromagnets. The core 9 is surrounded by a coil 11 and the coil 11 is covered by a metallic cover that should be made of magnetizable material so that it also provides for the magnetic field. Further, the core 9 has a central hole 10. At the gripping end of the gripper 1, a pipette tip mount 13 is attached to the hole 10 of the core and a vacuum tube 14 extends through the central hole 10 for providing vacuum for a pipette tip 17 that can be attacked to the pipette tip mount 13. The pipette can be used for aspirating and transfer of reagent or other liquid from an opened bottle or other vessel and same gripper can be used for handling the pipette tip and the caps of the bottles or other closures.

FIGS. 2a-2d show one embodiment of a reagent bottle and a schematic illustration of the gripper. The removal step of the caps can be seen in these figures. There are two closing caps on the reagent bottles 15. The outer cap 16 secures an inner cap 2 on its place during transport and long term storage. The outer cap 16 is removed by user before adding the reagent bottle into analyzer. In this embodiment the outer cap is connected to the bottle by a thread, but a removable plastic shrink seal or any other sealing method would be usable. The inner cap (shown as washer 4) is left on the bottle as it is and is detached by magnetic gripper 1 before aspiration.

Magnetic gripper 1 is used for decapping and capping. There is a metallic ring insert, the washer 4, in an inner cap 2 that interacts with a magnet. Advantage of the magnetic gripper is that it is possible to sense from current fed to magnet if cap is attached to the gripper. No additional sensors are needed. Detachment of the cap is done by feeding AC current into the magnet which will demagnetize metallic ring and magnetic force disappears.

Figure 2A:
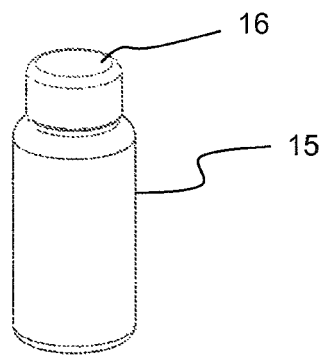
FIGS. 2*a*-2*d* are schematic illustrations of a sequence of opening and closing the reagent bottle.
Figure 2B:
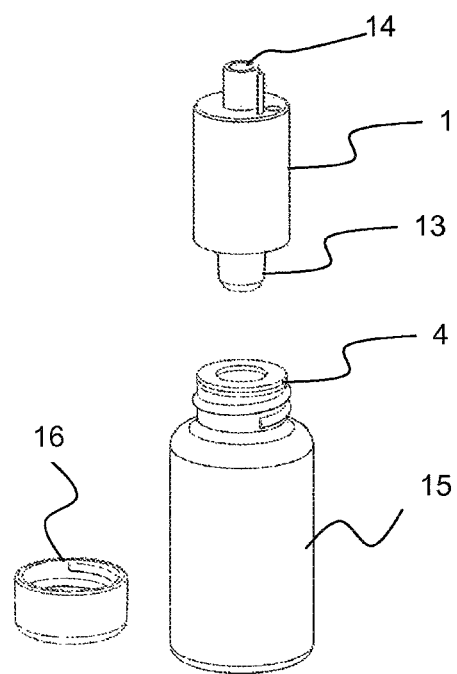
Figure 2C:
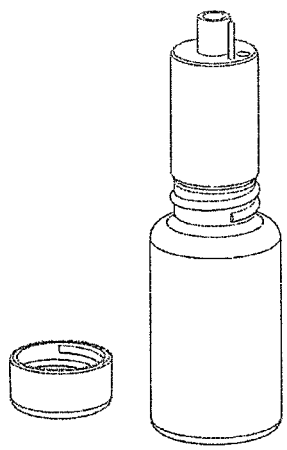
Figure 2D:
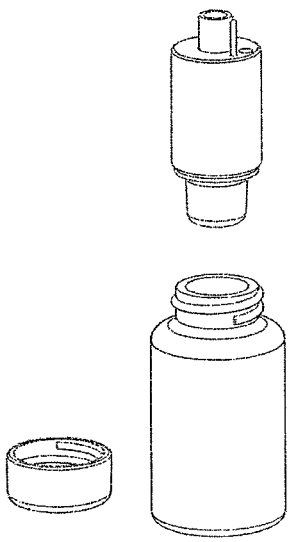

When reagent from the bottle 15 is needed, the gripper 1 is lowered on the cap and the pipette tip mount is inserted into the cap. It must be emphasized that if a pipette mount that extends from the gripper is used, a recess in the cap must be big enough in order to accommodate the mount 13. The pipette tip mount is preferably of described kind, since it would increase cost and make the device more complicated if the mount would be made retractable, for example. When the gripper is lowered on the washer 4, electric current is connected and a magnetic force connects the cap to the gripper and the cap 2 can be detached as seen in FIG. 2d. Now the cap can be lowered on a suitable place, detached using a demagnetizing step and a pipette tip attached to the gripper in similar manner. The pipette tip mount 13 is dimensioned to connect sealingly to the pipette tip thereby allowing aspiration of reagent by the pipette using suction or vacuum line 14. When desired amount of reagent is aspirated, the pipette tip is removed from the gripper and the cap is picked and set back to the mouth of the bottle.

The operation of the gripper is based on using electromagnet. Special methods are provided for ensuring properly functioning gripping, sensing and demagnetizing steps. They are discussed below and they form usable embodiments of the invention. These features may be combined with the invention based deformable cap shown in FIGS. 12 to 17.

Opening (detaching) and closing (attaching) the cap 2 may be carried out by electric magnet 9, 11, 12 and a cap 2 with metal upper surface 4 as described below. This method can be used together with a deformable cap.

1) The cap is caught by magnet driven by stepper motor control board. A metal washer 4 is inserted to the bottle cap 2. Now the magnet can grip the cap from the bottle 15. The magnet coil 11 of the magnet is driven with a stepper motor control PCBA (printed circuit board assembly). The circuit board of the stepper motor controls and measures the current of the stepper motor coil and therefore it can be readily used for driving the coil of the magnet also. Usually the control circuit boards include more available control circuits that are needed for operating the stepper motor in one direction, whereby drive and control for the electromagnet is readily available on the control circuit board of the motor.

2) Coil driver signal is a proper combination of DC and AC (100-500 Hz) signals to combine both good detection and to eliminate buzzer sound and vibration between cap and gripper. DC current is needed to form the magnetic field and bring enough force to keep the cap in touch with the gripper. AC current makes it possible to measure the change in impedance when cap touches the gripper. The AC+DC voltages are made by using special software for the stepper motor board. Normally PWM (pulse width modulation) adjusts proper current to the motor using current measuring circuits. In this case voltage is provided with PWM without any feedback. Therefore the current measuring circuit can be used for measuring current change in coil impedance and thus sensing the existence of cap. The main advantage is the capability of using normal stepper motor board and still be able to drive magnet and detect the existence and connection of the cap and the gripper.

3) The coil and magnetic circuit are designed so that the coil impedance of 100-500 Hz changes 20-30% when the washer of the cap is in touch with the gripper. So it's easy to detect whether the cap is on the gripper or not on basis of changing impedance. The proper working frequency is selected by the amount of change and possible noise related to the AC signal. 125 Hz will be a good choice between noise and sensing efficiency. The magnet construction uses both inner core and outer metal cover.

4) To disconnect the cap a demagnetizing process should be done in order to ensure fast and reliable disconnection. It includes a low frequency AC signal (2-100 Hz) with proper amplitude. A sequence of 10 cycles of 100 Hz signal with stepwise decreasing amplitude from 100% to 0% with 10% decrease after each cycle will provide good and fast demagnetizing.

As the magnetic gripper provides a way to handle reagent bottle caps and other closures, in some cases it is not possible to use magnetic gripper to grip a pipette tip or other liquid handling device reliably. One reason for this is that the seal between the pipette tip 17 and the mount 13 has to be gas tight to enable suction of liquid into the pipette tip 17. Also a magnet can interfere with other functions of the system. Therefore, a mechanical gripping method is provided for handling the caps 2, closures and liquid handling devices like pipette tips 17. This embodiment is described below referring to FIGS. 3-10.

Figure 3:
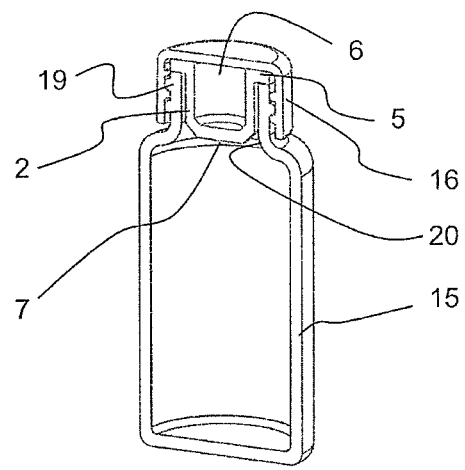
FIG. 3 is a sectional view of one embodiment of a reagent bottle.
Figure 4:
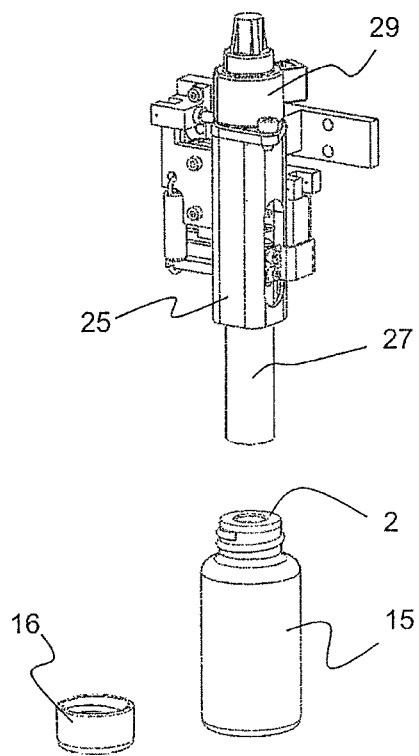
FIG. 4 shows a gripper and the reagent bottle in a first position.
Figure 5:
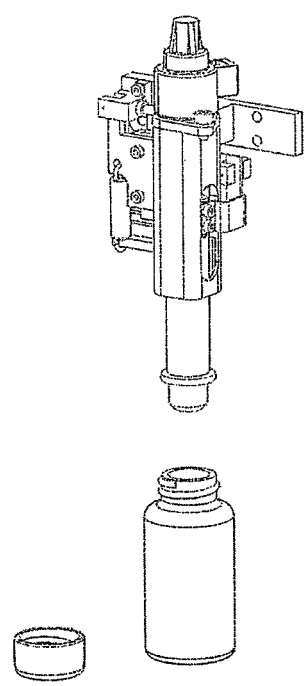
FIG. 5 shows the gripper and the bottle in a second position.

FIG. 3 shows an embodiment of a reagent bottle 15 that is closed by an outer sealing cap 16 and a removable and replaceable cap 2. The sealing cap 16 is mounted on the bottle by threads 19 and it is used for securing the liquid in the bottle during transport and storage. Removable cap 2 is pressed on the mouth of the bottle 15 by the sealing cap 16 and it can be even loosely fitted on the mouth of the bottle 15. For highly volatile substances a tighter fit may be needed, but a loose fit is often enough since the purpose of the cap is basically to prevent evaporation and seal of the lip 5 on the mouth of the bottle is often sufficient for that.

The cap 2 (see also FIG. 9) has a cylindrical body having an outer surface 8 that ends to a flat bottom surface 7 the cylindrical body part joins the bottom through a bevel 20. The bevel 20 assists inserting the cap on the bottle mouth. On the opposite end of the cap 2 is a circular collar 5 that is dimensioned to cover the mouth of the bottle 15. The top of the cap 2 on the side of the collar 5 has a recess 6 extending inside the cap. This recess 6 is dimensioned to accommodate the pipette mount 13 so that the mount 13 and the inner surface of the recess 6 and the outer surface of the pipette tip mount 13 form a tight cone joint. The recess 6 has a bevel 21 for guiding the pipette tip mount 13.

The cone joint needed for tight and reliably strong attachment of a pipette tip and the cap can be accomplished in many ways. It can be contemplated that the tip mount 13 and the recess have other form than circular, but then they should be always exactly orientated to each other during picking phase and manufacture of the pieces could be more expensive. When circular cross sections are used for both, the surfaces always match each other and the geometry is easy to manufacture. The conical joint with tight enough seal can be accomplished by dimensioning the bevel 21 of the recess and a bevel 22 of the pipette tip mount so that they form the cone joint, or using suitable conical shape on the inner side of the recess 6 of the cap 2 and the recess 6 of the pipette tip 17. Alternatively, the slightly conical shape can be made on the outer surface of the pipette tip mount 13 or both of these surfaces may be matchingly conical. The angles of the cones are determined by the gripping forces need and properties of the materials, for example friction coefficient and deformability. It is important that friction forces are sufficient for keeping the pipette tip attached during expelling the liquid from the tip.

The cap according to the invention is described in FIGS. 12 to 17. The features of this cap may be combined with features of caps described above, if desired. The cap 42 has a cylindrical body having a curved outer surface 8 that ends to a flat bottom surface 7. The outer surface has barrel shaped form that narrows towards the flat bottom surface 7. This barrel shape provides effective sealing surface on the mouth of a bottle making the cap very usable for sealing in even highly volatile liquids like methanol. The barrel shape that narrows towards the flat surface also assists inserting the cap on the bottle mouth. On the opposite end of the cap 42 is a circular collar 5 that is dimensioned to cover the mouth of the bottle 15. The top of the cap 42 on the side of the collar 5 has a recess 6 extending inside the cap. The upper surface of the collar is angled to slope from the outer rim 38 of the collar 5 towards the recess in order to form a conical sealing surface 39 so that the sealing surface 39 and the collar 5 extend away from the mouth of the recess. The truncoconical sealing surface 39 is therefore formed between an inner rim edge forming the opening of the cap and an outer rim edge arranged at a distance from the inner rim edge away from the bottom surface 7 of the cap 42. The resulting conical surface 39 therefore flares open away from the bottom surface 7 of the cap 42. According to one aspect, the inner rim edge of the sealing surface 39 defines a plane in respect to which the sealing surface 39 forms an angle in the range of 0 to 60 degrees upwards from the plane away from the bottom surface 7 of the cap 42. The opposite side of the collar in relation to the sealing surface 39 is set about the same angle.

The inner surface of the recess 6 has basically the same barrel shaped curvature as the outer surface. About on the middle of the inner surface is a curved relief 40. The inner surface 41 and the outer surface 8 form the body of the cap. This body part between the bottom of the cap and the rim is made at least partially of flexible material such as rubber, flexible plastic, silicone or rubber. Flexibility is defined herein so that the shape of the body can be deformed by subjecting the recess 6 to suction. The whole cap is preferably made of same flexible material in order to facilitate the function of the cap. Detaching and application of the cap is described further below.

Figure 8:
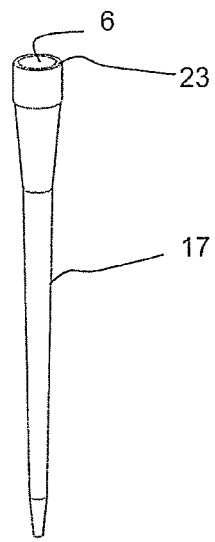
FIG. 8 shows a pipette tip.
Figure 9:
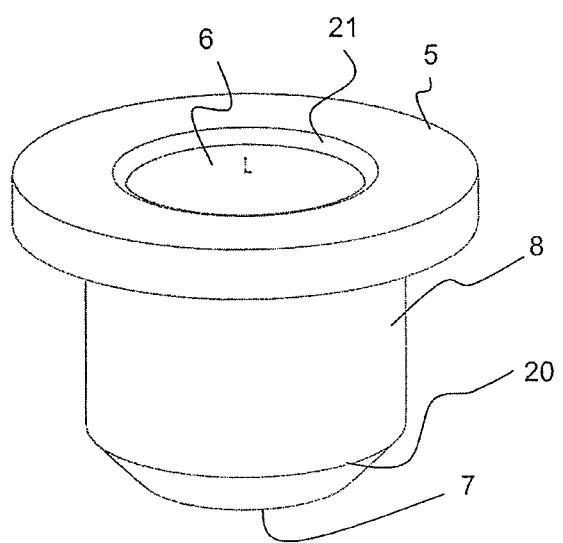
FIG. 9 shows a cap of the reagent bottle of FIGS. 4-6.

The pipette tip 17 shown in FIG. 8 has a similar recess 6 as the cap 2. The rim 23 of the tip has the same function as the lip 5 of the cap 2 during detachment from the mount 13. Otherwise the shape of the tip 23 is not part of the invention.

Figure 10:
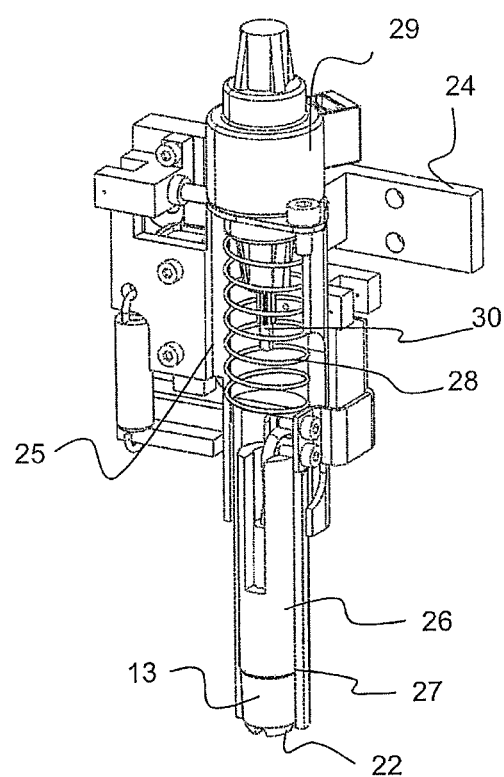
FIG. 10 is a sectional view of one embodiment of a gripper shown in FIGS. 4-7.

A gripper for handling above described caps and pipette tips is shown in FIG. 10.

The gripper is built on a body plate 24, via which it can be mounted on a robotic arm or other desired means that provide necessary free degrees of movement. The gripper body 25 is a tubular casing. In that casing 25 is slidably mounted the body 26 of the pipette tip and cap mount 13 (later a mount for short). The body 26 has a cylindrical outer surface and the mount 13 is attached at the free end of the body 26. The body is surrounded by a sleeve 27 that is slidably mounted inside the casing 25 so that the sleeve 27 slides within the casing 25 and the body 26 slide within the sleeve 27. The sleeve 27 has an open end wherefrom the mount 13 protrudes. On the opposite end of the sleeve is a spring 28 that allows the movement of the sleeve 27 over the body of the mount 13. The spring 28 is supported against the casing of an actuator 29. The actuator 29 closes one end of the gripper casing 25 and it has an operating pin 30 that extends inside the coil of the spring 28 and towards the end of the sleeve 27.

Figure 6:
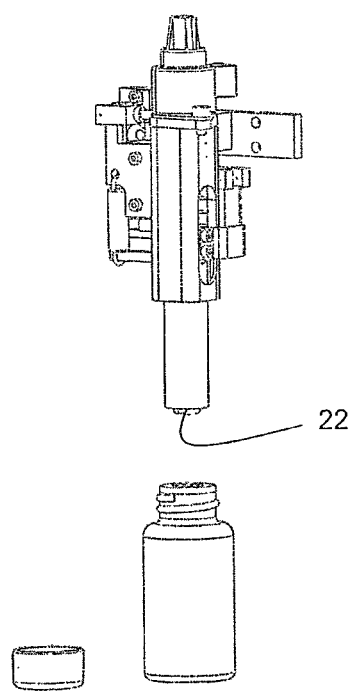
FIG. 6 shows the gripper and the bottle in third position.
Figure 7:
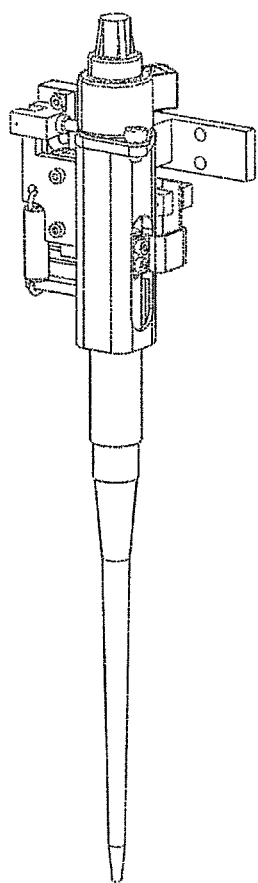
FIG. 7 shows a pipette tip attached to the gripper of FIGS. 4-6.

The operation of the gripper is shown in FIGS. 4-7. When the sealing cap 16 has been removed from the reagent bottle 15 or other vessel having a cap 2 according to the invention, the picking step of the cap 2 can be initiated. At that moment the sleeve 27 is pushed by the spring 30 over the mount 13 and covers it. The cap 2 is on the mouth of the bottle. When the mount 13 of the gripper is pushed over the lip 5 of the cap 2, the edges of the sleeve 27 contact the lip and are pushed away from over the mount 13 and against the spring 28. The mount 13 is pushed into the recess 6 of the cap 2 and a cone joint is formed between the mount and the cap 2. The gripper has suitable detectors for detecting secure attachment by movements of the mount 13 and the sleeve 27. When the contact has been made by cone joint contact, the cap may be picked up and transferred to a desired place. When the cap 2 is to be detached from the mount 13, the actuator 29 is activated whereafter the operating pin 30 is pushed against the end of the sleeve 27, which is pushed against the lip of the cap 2 and the cap 2 is detached from the mount 13. In FIG. 6 the cap has been detached and placed back on the mouth of the bottle 15.

The picking and releasing a pipette tip 17 is done in a similar way. When the pipette tip is attached, it can be used for both dispensing and aspirating liquids into and from opened vessels as needed.

One feature related to the pipette tip is indication of level of liquid. This can be done by measuring the capacitance of the frame of the apparatus and the tip at 1 MHz alternating current for example. When the tip contacts the liquid surface, the capacitance is altered and the level of the liquid can be indicated and used for calculations as needed.

The capacitance measurement means can be integrated into magnetic gripper or be provided separately.

Figure 11:
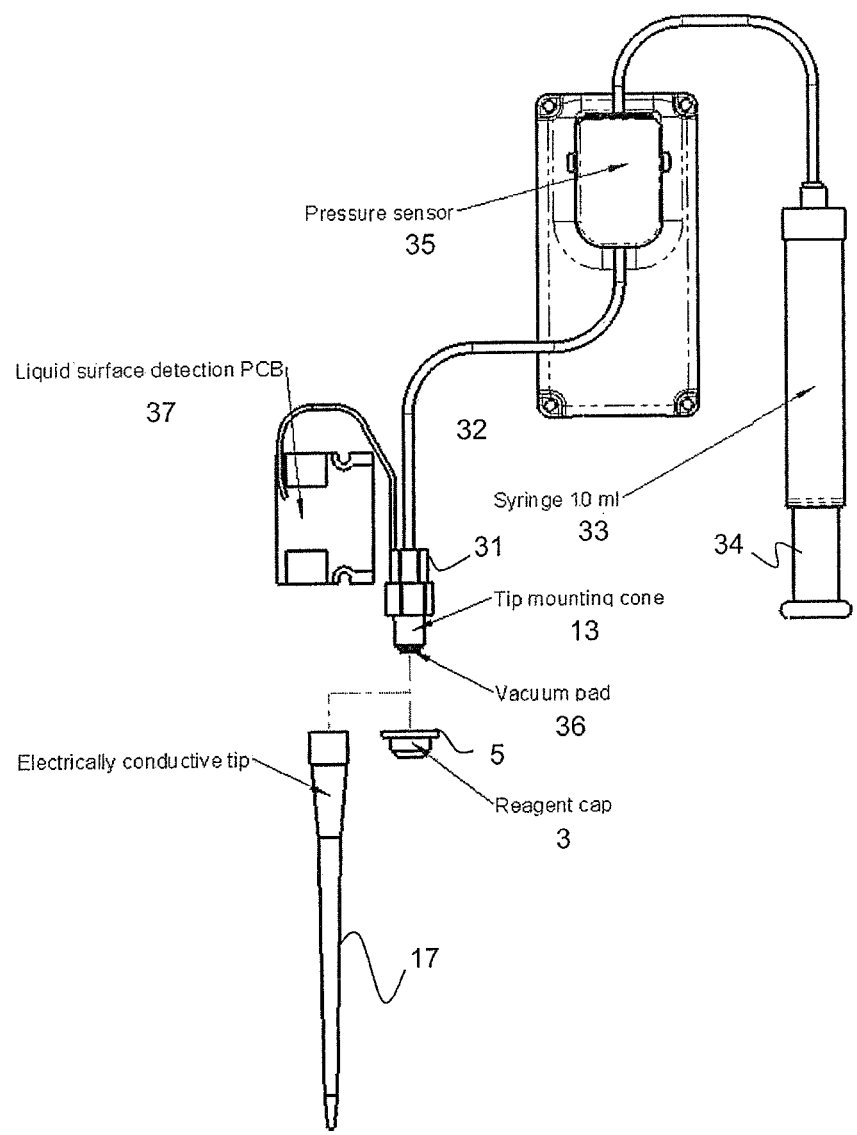
FIG. 11 shows a further embodiment of a gripper.
Figure 12:
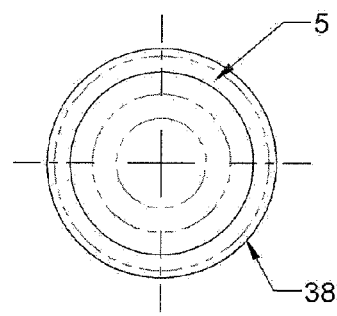
FIGS. 12 to 17 depict one embodiment of a cap according to the invention for a reagent bottle.
Figure 13:
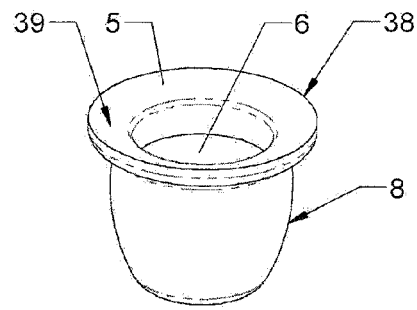
Figure 14:
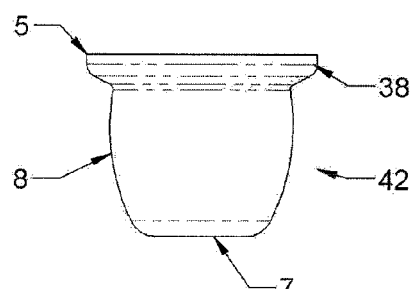
Figure 15:
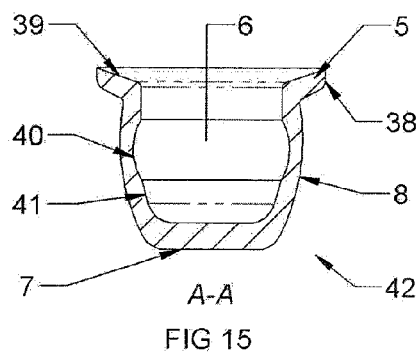
Figure 16:
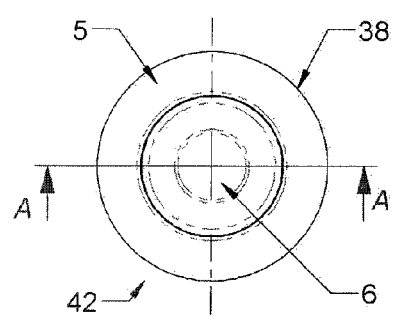

One further embodiment of the gripper is shown in FIG. 11. This gripper can be used in connection with any pipette tip 17 or a reagent bottle cap or closure described above. The gripper is built on a body 31 onto which is attached a pipette tip mount 13. This tip mount 13 is similar as those described above and provides same functions. At the free end of the pipette tip mount 13 is a vacuum pad 36. The vacuum pad 36 is joined to vacuum line 32 arranged through the tip mount 13 and body 31 and the line 31 leads to a syringe 33 through a pressure sensor 35. The vacuum is achieved by a plunger of the syringe 33. The syringe can be replaced by any suitable pumping apparatus. Further, a liquid surface detection device 37 is connected to the body 31. The assembly of pressure line, pressure sensor and syringe as well as liquid detection Printed Circuit Board (PCB) disclosed herein is one possible setup that can be used also in embodiments described earlier. Of course, any modifications within the claimed scope of the invention are possible.

When a reagent cap 3 is to be detached from a bottle, a robot is driven on the cap 3 and the vacuum pad 36 is lowered on the flat surface of the cap 3. The flat surface may be the upper surface of the rim 5. Thereafter a negative pressure is sucked in the vacuum pad 36 by the syringe 33. The negative pressure attaches the cap 3 to the cup 33. The cap is detached from the bottle and desired liquid dosages are performed. The cap is attached by driving the gripper 31 by the robot back at the top of the reagent bottle and pressing the cap on bottle. When cap is attached the plunger of the syringe can be pushed in, whereby the negative pressure is relieved and the cap detached from the gripper.

Figure 17:
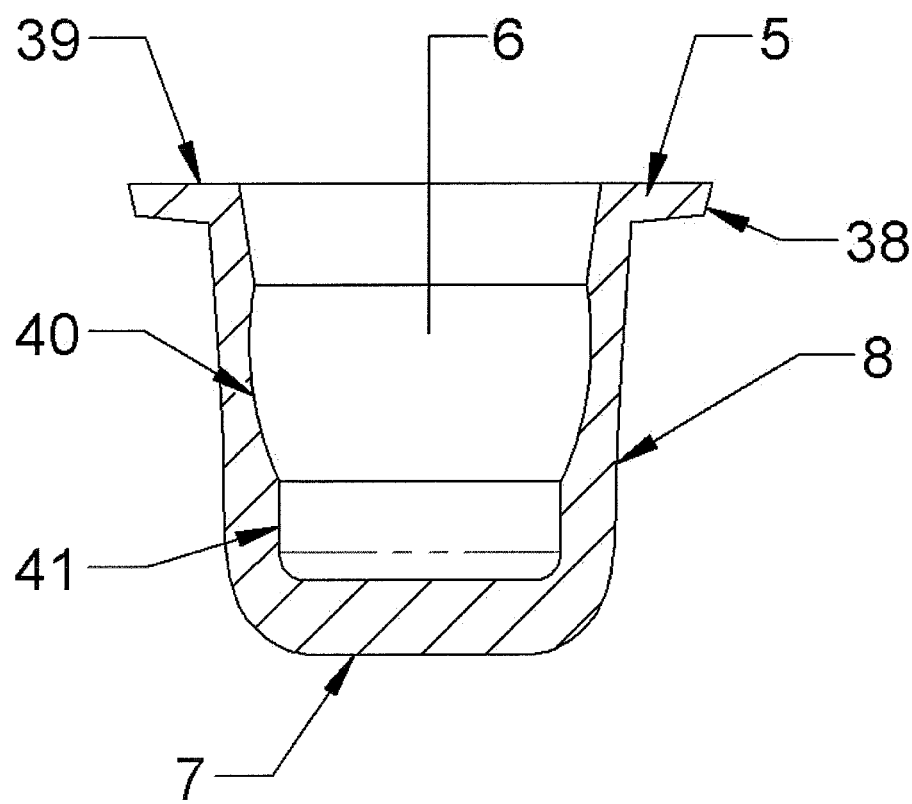
Figure 18:
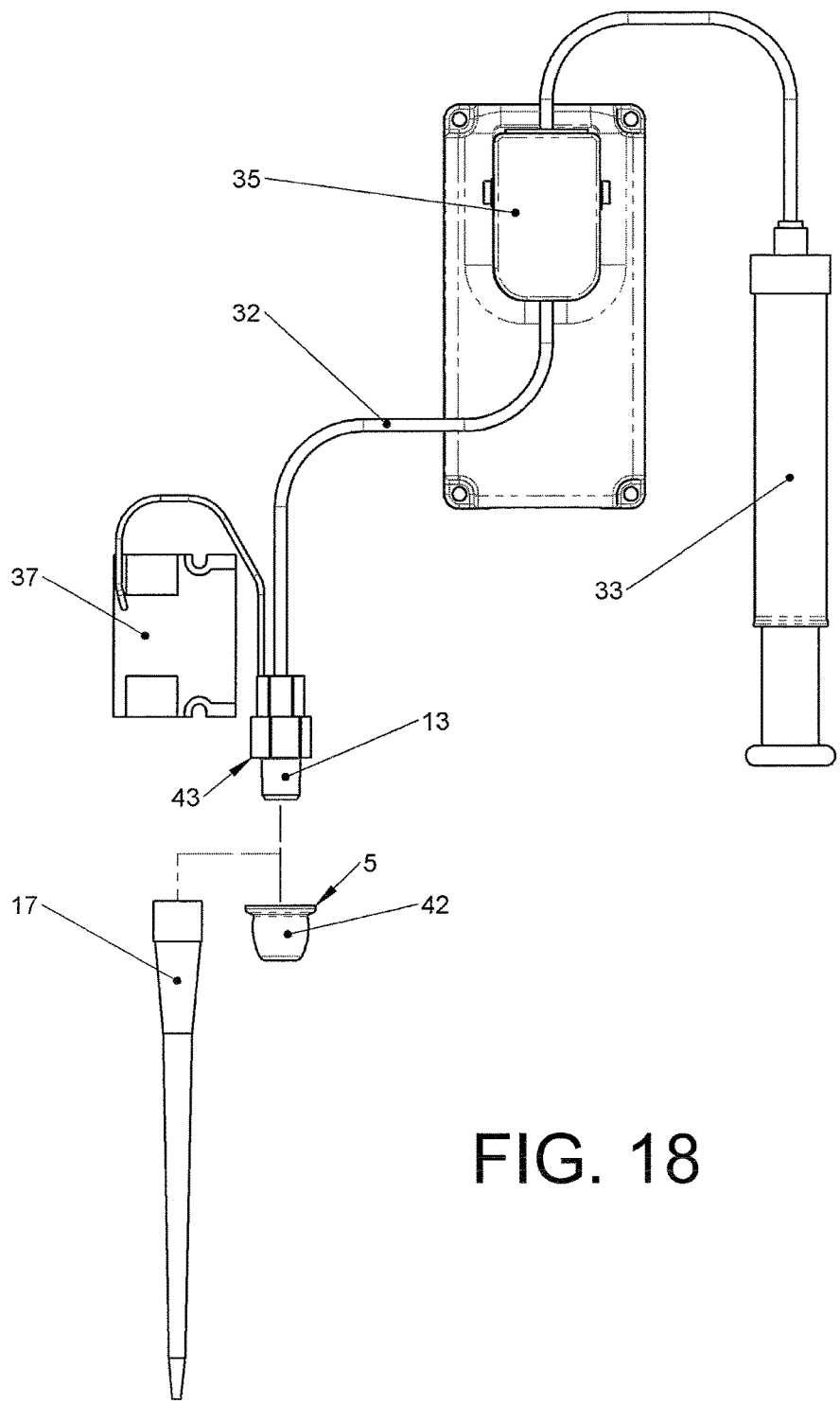
FIG. 18 shows a further embodiment of a gripper.

FIG. 18 shows a gripper that can be used for flexible caps according to the invention. This gripper differs from the grippers described above in that the vacuum pad is omitted. The tip mounting cone 13 may be dimensioned to fit in the recess 6 of the cap 42. In that case the tip mounting cone must be equipped with a rim 43 that extends over the collar 5 of the cap. Alternatively the end surface of the tip mounting cone should extend at least partially over the collar so that the opening of the recess 6 is covered. These surfaces form an attaching surface for the cap 42. When an attaching surface of the tip mounting cone is lowered over the sealing surface of the collar 5 of the cap 42, vacuum can be applied. The sealing surface is made smooth so that it forms an air tight seal over the attaching surface. When vacuum is applied, the angled collar 5 bends towards the attaching surface, that is preferably planar. The bending of the collar causes the flexible body of the cap 42 to move inwards. The inward movement of the body is enhanced by underpressure (pressure below ambient) inside the cap. The curved relief 40 facilitates the movement and positions the place of moment at the level of the relief. FIG. 17 depicts one inwardly bended form of a deformable cap shown in FIGS. 12-16. It is to be pointed out that compared to the embodiments shown in FIGS. 12 to 16, the exemplary cap shown in FIG. 17 is not illustrated in the same scale. When the sealing surface formed by the outer surface 8 of the cap 42 is moved inwards, seal between the neck of a bottle or other vessel is released and the cap may be lifted from the bottle. As can be noted, the suction accomplishes both release of the seal and force needed for lifting the cap 42. As the cap is released from the inner surface of the bottle neck, only minor force is needed for removing the cap.

According to another embodiment of the invention the collar 5 of the cap is rigid and the body is flexible. Angle of the sealing surface of the collar should match the angle of the attaching surface of the rim 43 of the tip mounting cone. When vacuum is applied the collar remains stationary and the cap body deforms inwards.

According to another embodiment of the invention the cap does not comprise a collar. The body is made of flexible material. The gripper comprises a vacuum pad for example as described in FIG. 11. The gripping interface is formed by the vacuum pad and the upper flat surface of the cap body.

When the cap is placed on a neck of a bottle or opening of some other vessel, releasing the suction lets the flexible body of the cap bulge outwards to its original shape whereby the outer surface forms a tight seal over the opening.

This provides effective gas tight seal that is needed for closing bottles containing volatile liquids, for example methanol.

The use of a pipette tip is similar as with magnetic gripper and mechanical gripper with grippers shown in FIGS. 11 and 18. A cone mount 13 around the vacuum pad is used for attachment of the pipette tip and the tip is attached for use by pressing the pipette tip to the cone in FIG. 11. The tip is removed at a separate withdrawal station or the tip can be pushed off by the detaching sleeve 27 of a mechanical gripper itself.

When magnetic or suction gripper is used, attachment of the pipette tip holding thereof has to be secured by special arrangement, for example by driving the tip through an optical fork. At the mechanical gripper the optical sensor of the detaching sleeve 27 indicates constantly the hold on the cap or tip.

The suction line includes a pressure sensor 35 for following formation of blocks in pipette during dispensing of liquid. This has been described above. By the same pressure sensor 35 operation of the vacuum pad or cap can be monitored and attachment of the cap detected. If the negative pressure suddenly disappears, detaching of the cap from the gripper is noticed. Pressure sensor can be used for indicating possible leaks in cap attachment or the cap.

The benefit of the suction gripper is that the system does not require other added mechanics than a vacuum pad. Even the vacuum pad may be integrated to the tip mounting cone as an attachment surface if a flexible cap 42 according to the invention is used. The syringe or pump, pressure sensor, cone attachment of the pipette tip and the suction line has to be built anyway for use of the pipette tip, especially if the tip is used for mixing whole blood as described in a patent application filed parallel with this application.

One benefit of using flexible caps and suction is that manufacturing tolerances of tube opening widths and the caps can be omitted. The body of the cap should be flexible enough to be able to compensate for the largest tolerated manufacturing value for the tube opening diameter to ensure effective gas tight sealing at all tolerated values. For example the variance in opening diameter may be about 0.5 mm for bottles with opening diameter of 13.2 mm. Alternatively, the variance in opening diameter may be about 4% of the opening diameter in rest position. With a cap body diameter of at least 13.5 mm at its widest point, the required minimum change in the cap body diameter would be about 1 mm or about 8%, i.e. about twice the amount of the tolerance to ensure proper sealing tightness. Forces applied to generate the vacuum would then be at the level of 0.1-0.9 bar, preferably about 0.5 bar.

In all embodiments described herein, the surface of the liquid is detected by using capacitive liquid level sensor and electrically conductive pipette tip. The surface could be detected also by measuring the pressure change caused by the surface.

It must be noted that mechanical structures of the above described elements and parts may vary as well as their geometrical shapes and dimensions.

Thus, while there have been shown and described and pointed out fundamental novel features of the invention as applied to a preferred embodiment thereof, it will be understood that various omissions and substitutions and changes in the form and details of the method and device may be made by those skilled in the art without departing from the spirit of the invention. For example, it is expressly intended that all combinations of those elements and/or method steps which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. A system comprising:
   a bottle with a mouth;
   a removable cap, the cap comprising a flexible body extending into the mouth of the bottle and having an inner recess, and a collar extending externally over the mouth of the bottle;
   a gripper, the gripper comprising a mounting cone configured to fit within the inner recess of the body of the cap and a rim configured to extend over the collar of the cap, the rim comprising an attaching surface for the cap; and
   a vacuum line within the mounting cone,
   wherein, when the mounting cone is inserted into the recess of the body of the cap and the rim is extended over the collar, a vacuum is applied to the cap, the vacuum being sufficient to cause the flexible body to move inwards thereby moving the collar toward the attaching surface, facilitating detachment of the cap from the bottle.

2. A system according to the claim 1, wherein a cone joint is formed between the mounting cone and the recess of the cap.

3. A system according to claim 1, wherein the system further comprises a pressure sensor.

4. A system according to claim 3, wherein the pressure sensor can indicate possible leaks in a seal between the gripping interface and the cap or in the cap.

5. A system according to claim 1, wherein the recess extends below the collar.

6. A method for removing a cap from a reagent bottle by a gripper, the gripper comprising an attaching surface that can form a seal with the cap, the method comprising:
   providing a bottle with a mouth and a cap comprising a body extending into the mouth of the bottle and having an inner recess, a bottom, and a collar surrounding an opening of the recess and extending externally over the mouth of the bottle, the body extending between the bottom and the collar, wherein at least part of the body is made of a flexible material that allows deformation of at least the body when suction is applied to the recess,
   inserting the gripper into the recess, the gripper having a mounting cone fitting within the recess of the body of the cap, the cone having a rim extending over the collar of the cap, the rim having the attaching surface for the cap,
   applying suction to the recess through the mounting cone sufficient to form a seal with the attaching surface,
   deforming the flexible body inwardly and moving the collar toward the attaching surface, and
   removing the cap from the bottle.

7. A method according to claim 6, wherein the deformation changes the cap body diameter at least 8%.

* * * * *